United States Patent [19]

Araki et al.

[11] 4,423,052

[45] Dec. 27, 1983

[54] 1,4-DIHYDROPYRIDINE-3,5-DICARBOXYLIC ACID ESTER DERIVATIVES

[75] Inventors: Kazuhiko Araki; Hideki Ao, both of Nakatsu; Kenichi Aihara, Yoshitomimachi; Tomohiko Kimura, Izumi, all of Japan

[73] Assignee: Yoshitomi Pharmaceutical Industries Ltd., Japan

[21] Appl. No.: 387,856

[22] PCT Filed: Oct. 2, 1981

[86] PCT No.: PCT/JP81/00262

§ 371 Date: Jun. 1, 1982

§ 102(e) Date: Jun. 1, 1982

[87] PCT Pub. No.: WO82/01185

PCT Pub. Date: Apr. 15, 1982

[30] Foreign Application Priority Data

Mar. 10, 1980 [JP] Japan ................................ 55/138940

[51] Int. Cl.$^3$ .................... C07D 213/55; A61K 31/44
[52] U.S. Cl. ..................................... 424/266; 546/321
[58] Field of Search ........................ 546/321; 424/266

[56] References Cited

U.S. PATENT DOCUMENTS 3,985,758 10/1976 Murakami et al. ................... 546/321
3,996,234 12/1976 Araki et al. .......................... 546/321

*Primary Examiner*—Alan L. Rotman
*Attorney, Agent, or Firm*—Larson and Taylor

[57] ABSTRACT

1,4-Dihydropyridine-3,5-dicarboxylic acid ester derivatives represented by the formula

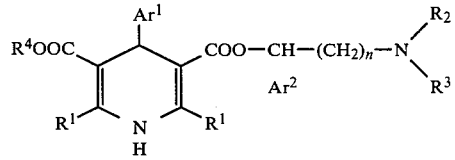

(wherein $Ar^1$ and $Ar^2$ are each the same or different and represent an aryl group; $R^1$ represents a lower alkyl group; $R^2$ and $R^3$ are each the same or different and represent a lower alkyl or aralkyl group; n is 1 or 2; and $R^4$ represents a lower alkyl) or the acid addition salts thereof. These compounds are useful as antihypertensive agents and as agents for treating the disturbances of cardiac or cerebral circulation.

11 Claims, No Drawings

1,4-DIHYDROPYRIDINE-3,5-DICARBOXYLIC ACID ESTER DERIVATIVES

TECHNICAL FIELD AND DISCLOSURE OF INVENTION

This invention relates to novel 1,4-dihydropyridine-3,5-dicarboxylic acid ester derivatives represented by the formula

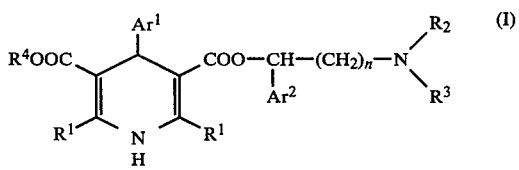

and the salts thereof both useful as pharmaceuticals and also concerns with processes for preparing them.

The symbols in the formula previously given each represent the following.

$Ar^1$ and $Ar^2$ are each the same or different and represent an aryl group (such as a phenyl group or a phenyl group having 1 to 3 substituents which are each the same or different and which include a halogen atom such as fluorine, bromine, chlorine, iodine or the like; a lower alkyl group such as methyl, ethyl, propyl, isopropyl, butyl or the like; a lower alkoxy group such as methoxy, ethoxy, propoxy, isopropoxy, butoxy or the like; a hydroxyl group; a nitro group; a cyano group; a methylenedioxy group; a trihalomethyl group such as trifluoromethyl, tribromomethyl, trichloromethyl or the like; a lower alkylamino group such as dimethylamino, diethylamino, dibutylamino or the like; a lower alkylthio group such as methylthio, ethylthio, propylthio, isopropylthio or the like; or a lower alkylsulfonyl group such as methylsulfonyl, ethylsulfonyl, propylsulfonyl, isopropylsulfonyl or the like.

$R^1$ represents a lower alkyl group (such as methyl, ethyl, propyl, isopropyl, butyl or the like).

$R^2$ and $R^3$ are each the same or different and represent a lower alkyl group (such as mentioned for $R^1$) or an aralkyl group (benzyl, phenethyl or the like optionally substituted with a halogen atom, a lower alkoxy group or the like on benzene ring such as benzyl, parafluorobenzyl, parachlorobenzyl, paramethoxybenzyl, 3,4-dichlorobenzyl, phenethyl, parachlorophenethyl, paramethoxyphenethyl, 3,4-dimethoxyphenethyl, etc.).
n is 1 or 2.

$R^4$ represents a lower alkyl group (such as mentioned for $R^1$).

According to the present invention, the compounds having the formula (I) are prepared, for examples, by any of the following processes.

Process 1

This process comprises reacting a compound of the formula:

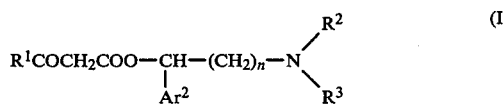

wherein the symbols are as defined above, with a compound of the formula:

wherein the symbol is as defined above, and a compound of the formula:

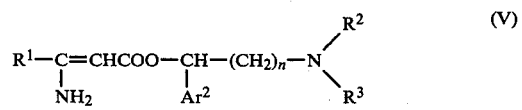

wherein $R^1$ is as defined above and $R^4$ is a lower alkyl group.

This reaction is carried out by mixing together the compounds of the formulae (II), (III) and (IV) and heating the mixture in the presence of an adequate solvent (such as methanol, ethanol, propanol, isopropanol, dioxane, benzene, toluene, acetonitrile, dimethylformamide, dimethylsulfoxide or the like). The compound of the formula (IV) can be prepared, for example, by reacting a compound of the formula $R^1$—$COCH_2COOR^4$ with ammonia. The compound of the formula (IV) is reacted, after or without isolation, with the compounds of the formulae (II) and (III), thereby producing the compound of the formula (I).

Process 2

This process comprises reacting a compound of the formula

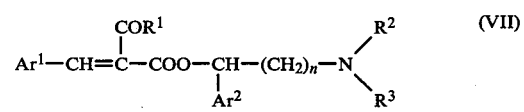

wherein the symbols are as defined above, with the compound of the formula (III) and a compound of the formula:

wherein the symbols are as defined above.

This reaction is conducted by mixing together the compounds of the formulae (V), (III) and (VI) and heating the mixture in the presence of a suitable solvent (such as mentioned above). The compound (V) can be prepared, for instance, by reacting the compound of the formula (II) with ammonia. The compound of the formula (V) is reacted, after or without isolation, with the compounds of the formulae (III) and (VI), thereby producing the compound of the formula (I).

Process 3

The process comprises reacting the compound of the formula (II) with the compound of the formula (III), and reacting the resulting compound of the formula:

$$Ar^1-CH=\underset{\underset{Ar^2}{|}}{\overset{\overset{COR^1}{|}}{C}}-COO-CH-(CH_2)_n-N\diagdown_{R^3}^{R^2} \quad (VII)$$

wherein the symbols are as defined above, with the compound of the formula (IV).

The reaction is effected by heating the compounds of the formulae (IV) and (VII) in the presence of a suitable solvent (such as mentioned above). The compound of the formula (VII) is reacted, after or without isolation, with the compound of the formula (IV).

Process 4

This process comprises reacting the compound of the formula (III) with the compound of formula (VI), and reacting the resulting compound of the formula

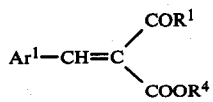  (VIII)

wherein the symbols are as defined above, with the compound of the formula (V).

The reaction is carried out by heating in the presence of an appropriate solvent (such as mentioned above). The compound of the formula (VIII) is reacted, after or without isolation, with the compound of the formula (V).

Process 5

This process comprises reacting a compound represented by the formula

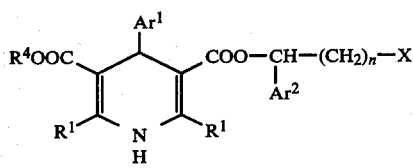  (IX)

wherein X is the acid residue of an active ester (such as chlorine, bromine, iodine or like halogen atoms or methylsulfonyloxy, ethylsulfonyloxy, benzenesulfonyloxy, paratoluensulfonyloxy or like alkyl- or aryl-sulfonyloxy or the like) and the other symbols are as defined above, with a compound represented by the formula

  (X)

wherein $R^2$ and $R^3$ are as defined above.

The reaction is performed in a suitable solvent (such as mentioned above) in the presence of an acid acceptor (such as alkali carbonate, alkali bicarbonate, alkali alcolate or like inorganic alkalis or triethylamine, dimethylaniline, diethylaniline, pyridine or like organic bases) at a temperature ranging approximately from room temperature to the boiling point of the solvent over a period of time between several hours and dozens of hours. The compound of the formula (IX) is easily prepared, for example, by any of the processes 1–4 from a compound of the formula

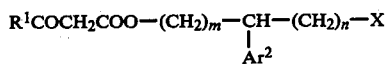  (XI)

wherein the symbols are as defined above.

Process 6

This process comprises reacting a compound represented by the formula

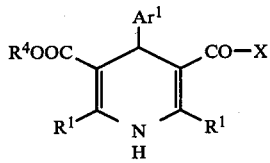  (XII)

wherein the symbols are as defined above, with a compound represented by the formula

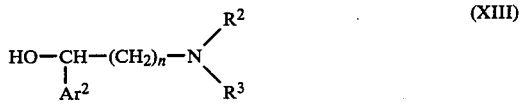  (XIII)

wherein the symbols are as defined above.

The reaction is effected in the same manner as described in the process 5.

The compound of the formula (I) thus prepared can be isolated and purified by the usual chemical procedure.

The compounds of this invention have asymmetric carbon atoms and include all classes of optical active compounds and mixtures thereof. A racemic compound is permitted, when required, to act on an optical active acid (such as tartaric acid, diacetyltartaric acid, tartranilic acid, dibenzoyltartaric acid, ditoluoyltartaric acid or the like) to form a diastereomer. The salt thereof is separated by crystallization, distillation, chromatography or any other suitable means and an optically active base is obtained from the salt. Compounds having the desired configuration can be stereo selectively prepared from an optically active compound serving as a starting material.

The compounds of this invention can be converted into hydrochloride, hydrobromide, phosphate, sulfate or like salts of inorganic acids, or oxalate, maleate, fumarate, tartarate, acetate or like salts of organic acids.

The compounds of this invention have high vasodilative and hypotensive activities and are useful as an antihypertensive agent and agents for treating the disturbances of cardiac or cerebral circulation.

Further the compounds of this invention, as compared with known compounds such as Nicardipine, are outstanding in hypotensive action and coronary and cerebral vasodilating actions and have an exceedingly long duration of action. Thus the present compounds are extremely useful for therapeutic purposes.

When used for pharmaceutical preparations, the compound of the present invention is mixed with a pharmacologically acceptable excipient, carrier, diluent or the like. The preparation thus obtained can be orally or parenterally administered in the form of tablets, capsules, granules, powders, injectable solutions or the like. Usually the daily dose for adults is about 1 to about 50 mg for oral administration. The preparation is daily given in single or divided doses, depending on the patient's age, body weight and/or the severity of the disease to be treated as well as the patient's response to the medication.

Pharmacological actions of the compounds of the invention are shown below.

(1) Hypotensive action

Method of measurement: Spontaneous hypertensive rats, 5 in each group, were used. The blood pressure was measured by an indirect tail cuff method. More specifically stated, the systolic pressure was measured by compressing the band until the pulsation of the artery in the tail has come to a stop. The test compounds were orally administered to the rats. The blood pressure was measured 5 hours after the administration of the test compound. Table 1 shows the results.

TABLE 1

| Test Compd. | Dose (mg/kg) | Hypotensive action |
| --- | --- | --- |
| Compound of* Example 1 | 1 | 26.0 ± 4.3 |
|  | 3 | 62.4 ± 10.8 |
| Nicardipine | 10 | 28.0 ± 3.4 |

*β-diastereoisomer (2) Increasing action of the cerebral blood flow

White rabbits, 4 in each group, were each paralyzed by intravenous administration of gallamine and mechanically ventilated so that the concentrations of blood gases were maintained at the normal level. The cerebral blood flow of a right hippocampus was measured by the hydrogen-clearance methods described in Circulation Research 14, 164 (1964) by Aukland et al. The test compounds were intravenously given. The cerebral blood flow increased after the administration of the compound was expressed in terms of percentage based on the blood flow before the administration thereof. Table 2 shows the increasing action of the cerebral blood flow and the duration of the action.

TABLE 2

| | Compound of Ex. 1* | Nicardipin |
| --- | --- | --- |
| | Dose (μg/kg) | |
| Time (minute) | 30 | 30 |
| 5 | 49.0 ± 11.2 (%) | 39.5 ± 5.9 (%) |
| 15 | 55.4 ± 3.9 | 13.8 ± 5.9 |
| 30 | 56.4 ± 5.4 | 18.0 ± 11.0 |
| 60 | 41.7 ± 3.4 | 8.5 ± 4.9 |
| 90 | 30.1 ± 7.4 | 6.8 ± 3.9 |

*β-diastereoisomer

The present invention is described hereinafter in detail with reference to the examples given below to which the invention, however, is not limited.

EXAMPLE 1

There are mixed together 15.6 g of acetoacetic acid 2-(N-benzyl-N-methylamino)-1-phenylethylester, 7.3 g of m-nitrobenzaldehyde, 5.5 g of β-aminocrotonic acid methyl ester and 150 ml of ethanol. The mixture is refluxed with heating for 16 hours. The reaction mixture is concentrated under reduced pressure. The residue is extracted with ethyl acetate and washed with water. The ethyl acetate is distilled off under reduced pressure. The residue is dissolved in acetone. To the solution is added saturated ethanolic hydrochloric acid. To the mixture is added a small amount of ether (in such amount that the resulting admixture becomes opaque) and the admixture is allowed to stand. The precipitated crystals are filtered off and recrystallized from ethanol, giving 5.0 g of 2,6-dimethyl-4-(m-nitrophenyl)-1,4-dihydropyridine-3,5-dicarboxylic acid-3methylester-5-[2-(N-benzyl-N-methylamino)-1-phenylethyl]ester hydrochloride as pale yellow crystals. M.p. 221° to 225° C. (decomposition). From the mother liquor is obtained another isomer (hydrochloride hemihydrate), melting at 181° to 183° C. (decomposition).

The product prepared in Example 1 is represented by the formula

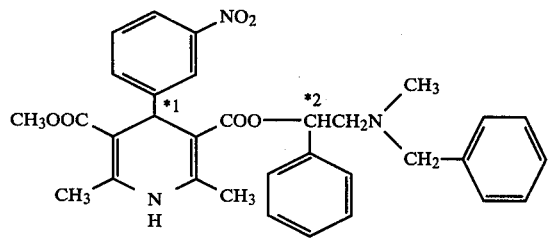

and have two asymmetric carbon atoms, and thus contains four isomers which are tabulated below. The product of the formula can be produced by subjecting to usual optical resolution the isomer with a melting point of 221° to 225° C. (β-diastereoisomer) and the other isomer with a melting point of 181° to 183° C. (α-diastereoisomer) both obtained above, or by using, starting materials in which one of the asymmetric carbon atoms marked "*1" and "*2" in the formula or both are optically active (when the disatereoisomer is obtained, this is separated).

| Isomer | Optical rotation | | Properties |
| --- | --- | --- | --- |
| | *1 | *2 | |
| (I) β-diastereoisomer | | | |
| 1 β1-isomer (hydrochloride hemihydrate) | − | + | Amorphous, $[\alpha]_D$ − 8.63 (c 0.5, methanol) |
| 2 β2-isomer (hydrochloride) | + | − | Amorphous, $[\alpha]_D$ + 13.04 (c 0.5, methanol) |
| (II) α-diastereoisomer | | | |
| 1 α1-isomer (hydrochloride hemihydrate) | + | + | M.p. 177–177.5° C. (decomposition) $[\alpha]_D$ − 152.72 (c 0.5, methanol) |
| 2 α2-isomer (hydrochloride | − | − | M.p. 176° C. (decomposition) $[\alpha]_D$ + 152.98 (c 0.5, methanol) |

EXAMPLE 2

Acetoacetic acid 2-(N-benzyl-N-methylamino)-1-(m-trifluoromethylphenyl)ethyl ester (18.5 g), 7.1 g of m-nitrobenzaldehyde, 5.4 g of β-aminocrotonic acid methyl ester and 150 ml of ethanol are mixed together and refluxed with heating for 20 hours. The reaction mixture is concentrated under reduced pressure, and the residue is extracted with ethyl acetate and washed with water. The ethyl acetate is distilled off under reduced pressure; the residue is dissolved in acetone; thereto are added saturated ethanolic hydrochloric acid and a small amount of ether (in such amount that the mixture becomes opaque) and the mixture is allowed to stand. The precipitated crystals are filtered off and recrystallized twice from ethanol, giving 4.5 g of 2,6-dimethyl-4-(m-nitrophenyl)-1,4-dihydropyridine-3,5-dicarboxylic acid-3-methylester-5-[2-(N-benzyl-N-methylamino)-1-(m-trifluoromethylphenyl)ethyl]ester hydrochloride as pale yellow crystals. Acetone is added to the highly viscous residue obtained by concentrating the mother liquor under reduced pressure, whereby crystals are formed. The crystals are filtered off and recrystallized from a small amount of ethanol, giving 4.0 g of the other diastereoisomer as pale yellow crystals, melting at 150° to 160° C. (decomposition).

Listed below are other compounds prepared in the same manner as in the examples given hereinbefore.

(1) 2,6-Dimethyl-4-(m-nitrophenyl)-1,4-dihydropyridine-3,5-dicarboxylic acid-3-methylester-5-[2-(N-benzyl-N-methylamino)-1-(p-nitrophenyl)ethyl]ester hydrochloride, M.p. 192°–195° C. (decomposition); the other isomer, M.p. 192°–195° C. (decomposition).

(2) 2,6-Dimethyl-4-(m-nitrophenyl)-1,4-dihydropyridine-3,5-dicarboxylic acid-3-methylester-5-[2-(N-benzyl-N-methylamino)-1-(p-fluorophenyl)ethyl]ester hydrochloride, M.p. 185°–180° C.; the other isomer, M.p. 227°–229° C. (decomposition).

(3) 2,6-Dimethyl-4-(m-nitrophenyl)-1,4-dihydropyridine-3,5-dicarboxylic acid-3-methylester-5-[2-(N-benzyl-N-methylamino)-1-(3,4-dichlorophenyl)ethyl]ester hydrochloride, M.p. 195°–197° C. (decomposition); the other isomer, M.p. 168°–171° C. (decomposition).

(4) 2,6-Dimethyl-4-(m-nitrophenyl)-1,4-dihydropyridine-3,5-dicarboxylic acid-3-methylester-5-[2-(N-benzyl-N-methylamino)-1-(3,4,5-trimethoxyphenyl)ethyl]ester hydrochloride, M.p. 204°–205° C. (decomposition).

(5) 2,6-Dimethyl-4-(m-nitrophenyl)-1,4-dihydropyridine-3,5-dicarboxylic acid-3-isopropylester-5-[2-(N-benzyl-N-methylamino)-1-phenylethyl]ester hydrochloride hemihydrate, M.p. 137°–139° C. (decomposition).

(6) 2,6-Dimethyl-4-(m-nitrophenyl)-1,4-dihydropyridine-3,5-dicarboxylic acid-3-methylester-5-[2-(N-benzyl-N-methylamino)-1-(p-chlorophenyl)ethyl]ester hydrochloride, M.p. 181°–184° C. (decomposition); the other isomer (hydrochloride monohydrate), M.p. 213°–216° C. (decomposition).

(7) 2,6-Dimethyl-4-(m-nitrophenyl)-1,4-dihydropyridine-3,5-dicarboxylic acid-3-methylester-5-[2-(N-benzyl-N-methylamino)-1-(p-tolyl)ethyl]ester hydrochloride hemihydrate, M.p. 183°–187° C. (decomposition); the other isomer (hydrochloride hemihydrate), M.p. 217°–222° C. (decomposition).

(8) 2,6-Dimethyl-4-(m-nitrophenyl)-1,4-dihydropyridine-3,5-dicarboxylic acid-3-methylester-5-[2-(N-benzyl-N-methylamino)-1-(2,3-dichloro-4-methoxyphenyl)ethyl]ester hydrochloride, M.p. 221°–224° C. (decomposition); the other isomer (base), M.p. 199°–201° C.

(9) 2,6-Dimethyl-4-(m-nitrophenyl)-1,4-dihydropyridine-3,5-dicarboxylic acid-3-methylester-5-[2-(N-(3,4-dimethoxyphenethyl)-N-methylamino)-1-phenylethyl]ester hydrochloride monohydrate, M.p. 125°–128° C. (decomposition).

(10) 2,6-Dimethyl-4-(o-nitrophenyl)-1,4-dihydropyridine-3,5-dicarboxylic acid-3-methylester-5-[2-(N-benzyl-N-methylamino)-1-phenylethyl]ester hydrochloride monohydrate, M.p. 226°–228° C. (decomposition).

(11) 2,6-Dimethyl-4-(o-cyanophenyl)-1,4-dihydropyridine-3,5-dicarboxylic acid-3-methylester-5-[2-(N-benzyl-N-methylamino)-1-phenylethyl]ester hydrochloride, M.p. 233°–234° C. (decomposition).

(12) 2,6-Dimethyl-4-(m-nitrophenyl)-1,4-dihydropyridine-3,5-dicarboxylic acid-3-methylester-5-[3-(N-benzyl-N-methylamino)-1-phenylpropyl]ester hydrochloride, pale yellow oil, thin-layer chromatography silica gel by Merck (Silica gel 60F 254): Rf=0.60 and 0.53 (ethyl acetate).

(13) 2,6-Dimethyl-4-(2,3-dichlorophenyl)-1,4-dihydropyridine-3,5-dicarboxylic acid-3-methylester-5-[2-(N-benzyl-N-methylamino)-1-phenylethyl]ester.

(14) 2,6-Dimethyl-4-(m-trifluoromethylphenyl)-1,4-dihydropyridine-3,5-dicarboxylic acid-3-ethylester-5-[2-(N-benzyl-N-methylamino)-1-phenylethyl]ester.

(15) 2,6-Dimethyl-4-(o-trifluoromethylphenyl)-1,4-dihydropyridine-3,5-dicarboxylic acid-3-ethylester-5-[2-(N-benzyl-N-methylamino)-1-phenylethyl]ester.

(16) 2,6-Dimethyl-4-(m-nitrophenyl)-1,4-dihydropyridine-3,5-dicarboxylic acid-3-methylester-5-[2-(N-benzyl-N-methylamino)-1-(p-hydroxyphenyl)ethyl]ester.

(17) 2,6-Dimethyl-4-(m-nitrophenyl)1,4-dihydropyridine-3,5-dicarboxylic acid-3-methylester-5-[2-(N-benzyl-N-methylamino)-1-(3,4-methylenedioxyphenyl)ethyl]ester.

(18) 2,6-Dimethyl-4-(m-nitrophenyl)-1,4-dihydropyridine-3,5-dicarboxylic acid-3-methylester-5-[2(N-benzyl-N-methylamino)-1-(p-isopropylthiophenyl)ethyl]ester.

(19) 2,6-Dimethyl-4-(m-nitrophenyl)-1,4-dihydropyridine-3,5-dicarboxylic acid-3-methylester-5-[2-(N-benzyl-N-methylamino)-1-(p-methylsulfonylphenyl)ethyl]ester.

(20) 2,6-Dimethyl-4-(m-nitrophenyl)-1,4-dihydropyridine-3,5-dicarboxylic acid-3-methyleste-5-[2-(N-benzyl-N-methylamino)-1-(p-dimethylaminophenyl)ethyl]ester.

(21) 2,6-Dimethyl-4-(m-nitrophenyl)-1,4-dihydropyridine-3,5-dicarboxylic acid-3-methylester-5-[2-(N-benzyl-N-methylamino)-1-(p-cyanophenyl)ethyl]ester.

(22) 2,6-Dimethyl-4-(m-nitrophenyl)-1,4-dihydropyridine-3,5-dicarboxylic acid-3-ethylester-5-[2-(N-benzyl-N-methylamino)-1-phenylethyl]ester.

Although the present invention is described in detail hereinbefore, namely in the specification and the examples contained therein, other embodiments and modification of the invention are possible without departing from the spirit and scope of the invention.

We claim:

1. 1,4-Dihydropyridine-3,5-dicarboxylic acid ester derivatives represented by the formula:

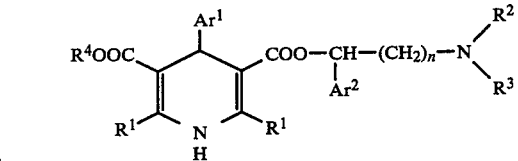

wherein $Ar^1$ and $Ar^2$ are each the same or different and represent phenyl group which may be substituted by 1 to 3 substituents on the benzene ring, each substituent being independently selected from halogen atom, $C_{1-4}$ alkyl group, $C_{1-4}$ alkoxy group, hydroxyl group, nitro group, cyano group, methylenedioxy group, trihalomethyl group, di-$C_{1-4}$ alkylamino group, $C_{1-4}$ alkylthio group and $C_{1-4}$ alkylsulfonyl group; $R^1$ represents $C_{1-4}$ alkyl group; $R^2$ and $R^3$ are each the same or different and represent $C_{1-4}$ alkyl group or phenyl-$C_{1-2}$ alkyl group which may be substituted by 1 or 2 substituents on the benzene ring, each substituent being selected from halogen atom or $C_{1-4}$ alkoxy group; n is 1 or 2; and $R^4$ represents $C_{1-4}$ alkyl group; or the pharmaceutically acceptable acid addition salts thereof.

2. The compound as defined in claim 1 which is 2,6-dimethyl-4-(m-nitrophenyl)-1,4-dihydropyridine-3,5- dicarboxylic acid-3-methylester-5-[2-(N-benzyl-N-methylamino)-1-phenylethyl]ester.

3. The compound as defined in claim 1 which is 2,6-dimethyl-4-(m-nitrophenyl)-1,4-dihydropyridine-3,5-dicarboxylic acid-3-isopropylester-5-[2-(N-benzyl-N-methylamino)-1-phenylethyl]ester.

4. The compound as defined in claim 1 which is 2,6-dimethyl-4-(o-nitrophenyl)-1,4-dihydropyridine-3,5-dicarboxylic acid-3-methylester-5-[2-(N-benzyl-N-methylamino)-1-phenylethyl]ester.

5. The compound as defined in claim 1 which is 2,6-dimethyl-4-(m-nitrophenyl)-1,4-dihydropyridine-3,5-dicarboxylic acid-3-methylester-5-[2-(N-benzyl-N-methylamino)-1-(p-fluorophenyl)ethyl]ester.

6. The compound as defined in claim 1 which is 2,6-dimethyl-4-(m-nitrophenyl)-1,4-dihydropyridine-3,5-dicarboxylic acid-3-methylester-5-[2-(N-benzyl-N-methylamino)-1-(p-chlorophenyl)ethyl]ester.

7. The compound as defined in claim 1 which is 2,6-dimethyl-4-(m-nitrophenyl)-1,4-dihydropyridine-3,5-dicarboxylic acid-3-methylester-5-[2-(N-benzyl-N-methylamino)-1-(3,4-dichlorophenyl)ether]ester.

8. The compound as defined in claim 1 which is 2,6-dimethyl-4-(m-nitrophenyl)-1,4-dihydropyridine-3,5-dicarboxylic acid-3-methylester-5-[2-(N-benzyl-N-methylamino)-1-(p-tolyl)ethyl]ester.

9. The compound as defined in claim 1 which is 2,6-dimethyl-4-(m-nitrophenyl)-1,4-dihydropyridine-3,5-dicarboxylic acid-3-methylester-5-[3-(N-benzyl-N-methylamino)-1-phenylpropyl]ester.

10. An antihypertensive composition comprising a compound of claim 1 in combination with an inert pharmaceutically acceptable excipient, said compound being present in a therapeutically effective amount.

11. A pharmaceutical composition for treating the disturbances of cardiac or cerebral circulation comprising a compound of claim 1 in combination with an inert pharmaceutically acceptable excipient, said compound being present in a therapeutically effective amount.

* * * * *